US012607615B2

(12) United States Patent
Mou et al.

(10) Patent No.: US 12,607,615 B2
(45) Date of Patent: Apr. 21, 2026

(54) REGULATION-DEVICE CONTROL CIRCUIT OF GAS DETECTION MODULE

(71) Applicant: Microjet Technology Co., Ltd., Hsinchu (TW)

(72) Inventors: Hao-Jan Mou, Hsinchu (TW); Yung-Chang Chen, Hsinchu (TW); Chi-Feng Huang, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 326 days.

(21) Appl. No.: 18/403,165

(22) Filed: Jan. 3, 2024

(65) Prior Publication Data

US 2025/0180529 A1 Jun. 5, 2025

(30) Foreign Application Priority Data

Dec. 1, 2023 (TW) .................................. 112146934

(51) Int. Cl.
*G01N 33/00* (2006.01)
*F24F 8/10* (2021.01)

(52) U.S. Cl.
CPC ........... *G01N 33/0027* (2013.01); *F24F 8/10* (2021.01)

(58) Field of Classification Search
CPC ........... G01N 33/0027; G01N 33/0009; G01N 33/0032; G01N 33/0073; F24F 8/10; G05B 19/0423; G05B 2219/24215
See application file for complete search history.

(56) References Cited

U.S. PATENT DOCUMENTS

2017/0147367 A1* 5/2017 Alley ................... G05B 19/054
2019/0018377 A1* 1/2019 Potucek .............. H04L 61/5038

FOREIGN PATENT DOCUMENTS

CN 105805885 A 7/2016
CN 206039816 U 3/2017
CN 207319010 U 5/2018
CN 110265111 A 9/2019
CN 111796057 A 10/2020
CN 113848794 A 12/2021
CN 215415186 U 1/2022

OTHER PUBLICATIONS

European Search Report for European Application No. 24151597.2, dated Jul. 12, 2024.
Yuniarto et al., "Developing IoT Wireless Sensor Network for Respiration Storage Chamber", 2023 17th International Conference on Telecommunication Systems, Services, and Applications (TSSA), IEEE, Oct. 12, 2023, XP034507405, 5 pages total.

* cited by examiner

*Primary Examiner* — Tarun Sinha
(74) *Attorney, Agent, or Firm* — Birch, Stewart, Kolasch & Birch, LLP

(57) ABSTRACT

A regulation-device control circuit of a gas detection module is disclosed and includes an AC power line, a power converter unit, plural voltage modulation components, a microcontroller unit, at least one expansion port, a data transmission line and an input and output control line. The regulation-device control circuit of a gas detection module is combined with each indoor circulating filtering device to implement air pollution detection, and cooperated the regulation operation.

19 Claims, 2 Drawing Sheets

REGULATION-DEVICE CONTROL CIRCUIT OF GAS DETECTION MODULE

CROSS-REFERENCE TO RELATED APPLICATION

This application claims priority to Taiwan Patent Application No. 112146934, filed on Dec. 1, 2023. The entire contents of the above-mentioned patent application are incorporated herein by reference for all purposes.

FIELD OF THE INVENTION

The present disclosure relates to a regulation-device control circuit of a connection device in an indoor air cleaning system, and more particularly to a regulation-device control circuit of a gas detection module.

BACKGROUND OF THE INVENTION

Suspended particles are solid particles or droplets contained in the air. Due to their extremely fine size, the suspended particles may enter the lungs of human body through the nasal hair in the nasal cavity easily, causing inflammation in the lungs, asthma or cardiovascular disease. If other pollutant compounds are attached to the suspended particles, it will further increase the harm to the respiratory system. In recent years, the problem of air pollution is getting worse. In particular, the concentration of particle matters (e.g., PM2.5) is often too high. Therefore, the monitoring to the concentration of the gas suspended particles is taken more and more seriously. However, the gas flows unstably due to the variable wind direction and the air volume, and the general gas-quality monitoring station is located in a fixed place. Under this circumstance, it is impossible for people to check the concentration of suspended particles in current environment.

Furthermore, in recent years, modern people are placing increasing importance on the quality of the air in their surroundings. For example, carbon monoxide, carbon dioxide, volatile organic compounds (VOC), PM2.5, nitric oxide, sulfur monoxide and even the suspended particles contained in the air are exposed in the environment to affect the human health, and even endanger the life seriously. Therefore, the quality of environmental air has attracted the attention of various countries. At present, how to detect the air quality and avoid the harm is a crucial issue that urgently needs to be solved.

In order to confirm the quality of the air, it is feasible to use a gas sensor to detect the air surrounding in the environment. If the detection information can be provided in real time to warn the people in the environment, it is helpful of avoiding the harm and facilitates the people to escape the hazard immediately, preventing the hazardous gas exposed in the environment from affecting the human health and causing the harm. Therefore, it is considered a valuable application to use a gas sensor to detect the air in the surrounding environment.

In addition, it is not easy to control the indoor air quality. Besides the outdoor air quality, the indoor air-conditioning conditions and the pollution sources are the major factors affecting the indoor air quality. It is necessary to intelligently and quickly detect indoor air pollution sources in various indoor fields, effectively remove the indoor air pollution to form a clean and safe breathing gas state, and monitor indoor air quality in real time anytime, anywhere. Certainly, if the concentration of the suspended particles in the indoor space field is strictly controlled according to the "clean room" standard, it allows to avoid the introduction, generation and retention of suspended particles, and the temperature and humidity in the indoor space field are controlled within the required range. That is to say, the number of suspended particles in the air pollution of the indoor space field is used to distinguish their classifications, so that it allows the indoor space field to meet the clean room requirements for safe breathing.

At present, the air pollution detection of the indoor air purification system is implemented by the gas detector to transmit the air pollution information, and then the air pollution information is transmitted to the cloud computing service device through the Internet of Things communication, so that the air pollution information of the outdoor field and the indoor field is stored to form a big data database of air pollution data. Based on the intelligent calculation and comparison of the big data database of air pollution data, a control command is intelligently selected to be sent to the fan of the circulating filtering device to start the regulation operation. In that, an internal circulation directed airflow is continuously generated in the indoor filed, and the air pollution is directed multiple times through the filter element to be filtered and removed, so that the gas state in the indoor filed has suspended particles meeting a specific specification quantity to reach a cleanliness of clean room.

In addition, the indoor air cleaning system includes multiple indoor cleaning devices and regulation devices arranged in the indoor field to regulate coordinately to achieve real-time monitoring of indoor air quality and real-time processing, filtering and cleaning. It makes the indoor air pollution completely clean and a clean and safe breathing gas state is formed. Therefore, how to regulate the above-mentioned cleaning and filtering devices in conjunction with the gas detector and cloud computing service device is the main subject of the present disclosure.

SUMMARY OF THE INVENTION

One object of the present disclosure is to provide a regulation-device control circuit of a gas detection module, which is combined with the devices on each indoor cleaning device to implement air pollution detection and coordinate the regulation operations. The control instructions are generated in the cloud computing service device to feed back to the gas detection module for electrical connection, and then transmitted to the driving and control element of the indoor cleaning device to regulate the device for starting operations. It allows the air pollution to pass therethrough for filtration, so that the gas state in the indoor field has the air pollution to be cleaned completely to meet the clean room requirements for safe breathing. In addition, the sensing element in the gas detection module autonomously calculating and comparing the air pollution information is connected to and issues the control instruction to the driving and control element the indoor clean device to regulate the starting operation. It allows the air pollution to pass through the filtration, so that the gas state in the indoor field has the air pollution to be cleaned completely to meet the clean room requirements for safe breathing, and an indoor air cleaning system is achieved.

In accordance with an aspect of the present disclosure, a regulation-device control circuit of a gas detection module is provided, and includes an AC power line, a power converter unit, a plurality of voltage modulation components and a microcontroller unit (MCU). The AC power line provides an AC voltage. The AC voltage outputted by the AC power line is inputted to the power converter unit to convert into a first DC voltage output through a plurality of first voltage dividing lines. The first DC voltage converted by the plurality of first voltage dividing lines of the power converter unit is inputted to the plurality of voltage modulation components and then modulated to output a second DC voltage through a plurality of second voltage dividing lines. The microcontroller unit (MCU) is connected to the second voltage dividing line, and the second DC voltage modulated by the second voltage dividing line is inputted to the microcontroller unit for operation. The microcontroller unit includes at least one expansion port, a data transmission line and an input and output control line. Each of the at least one expansion port is respectively connected to a sensing element to input a serial communication (IIC) signal to the microcontroller unit through a plurality of serial communication lines connected thereto for calculation, and a Universal Asynchronous Transceiver and Transceiver (UART) signal and a General Purpose Input and Output (GP I/O) signal are outputted for regulation. The data transmission line outputs a plurality of the Universal Asynchronous Transceiver and Transceiver (UART) signals for transmitting to an ultraviolet (UV) lamp device, at least one external regulation device, a wireless communication module and a communication interface device connected thereto. The input and output control line outputs the General Purpose Input and Output (GP I/O) signal for transmitting to the connected ultraviolet lamp device and the at least one external regulation device. Thereby, the wireless communication module is connected to the second voltage dividing line to input the second DC voltage converted, modulated and outputted therefrom according to a required DC voltage, and cooperates with the microcontroller unit to output the Universal Asynchronous Transceiver and Transceiver (UART) signal and the General Purpose Input and Output (GP I/O) signal for controlling activation and externally receiving communication signals. The communication interface device is connected to the first voltage dividing line to input the first DC voltage converted, modulated and outputted therefrom according to a required DC voltage, and cooperates with the microcontroller unit to output the Universal Asynchronous Transceiver and Transceiver (UART) signal for controlling activation and providing communication connections. The ultraviolet (UV) lamp device is connected to input the AC voltage (AC) outputted by the AC power line and cooperates with the microcontroller unit to output the General Purpose Input and Output (GP I/O) signal for controlling activation and regulation. The external regulation device is connected to input the AC voltage (AC) outputted by the AC power line, connected to the first voltage dividing line to input the first DC voltage converted therefrom according to a required DC voltage, and cooperates with the microcontroller unit to output the Universal Asynchronous Transceiver and Transceiver (UART) signal and the General Purpose Input and Output (GP I/O) signal for controlling activation and externally receiving communication signals for controlling activation and regulation.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

In order to realize an indoor air cleaning system, the present disclosure arranges a plurality of indoor cleaning devices and regulation devices in the room to coordinate and regulate to achieve real-time monitoring of indoor air quality and real-time processing and filtration and cleaning, so that the indoor air pollution is cleaned completely to form a clean and safe breathing gas state. Moreover, a regulation-device control circuit of a gas detection module is provided in combination with each indoor cleaning device and regulation device to implement air pollution detection and coordinate the regulation operations.

The present disclosure provides a regulation-device control circuit of a gas detection module, which includes: an AC power line, a power converter unit, a plurality of voltage modulation components, a microcontroller unit (MCU), at least one expansion port, a data transmission line and an input and output control line to implement air pollution detection and coordinate the regulation operations.

Figure 1:
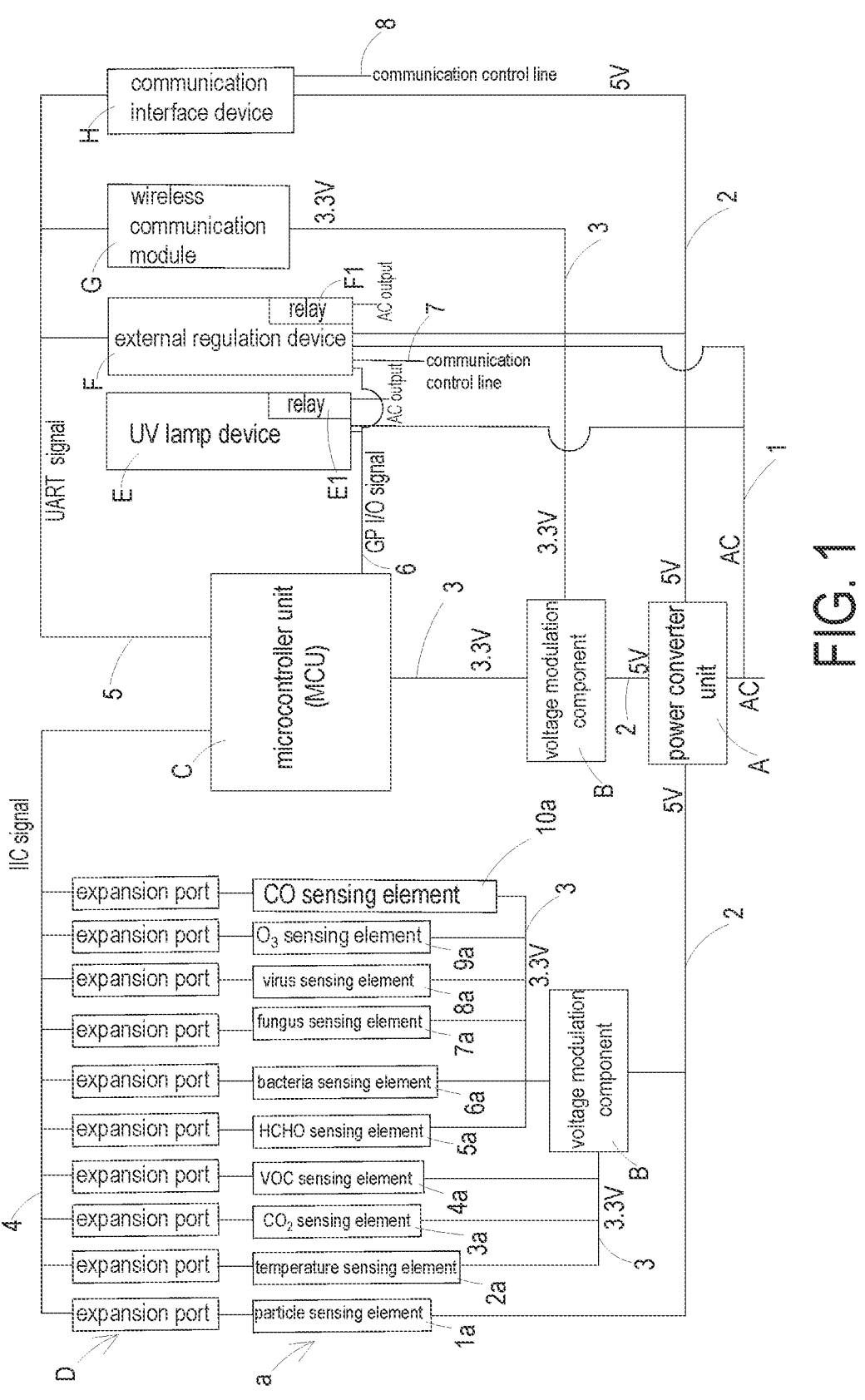
FIG. 1 is a schematic diagram illustrating a regulation-device control circuit of a gas detection module according to an embodiment of the present disclosure.
Figure 3:
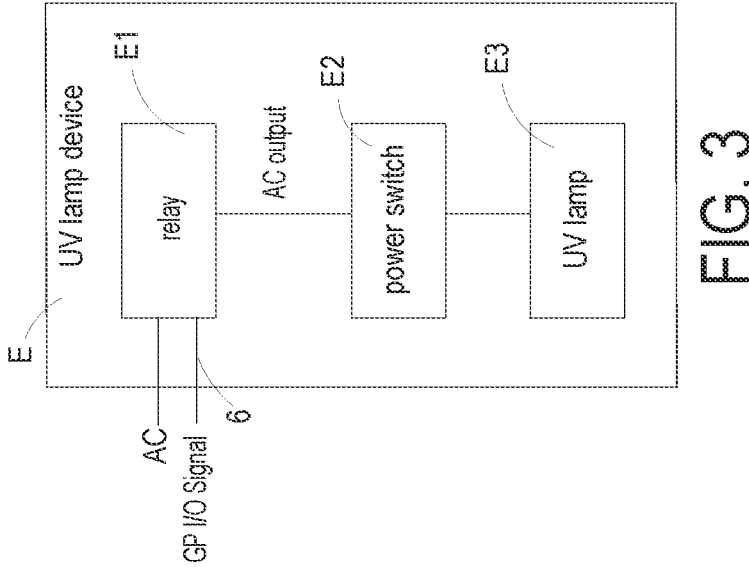
FIG. 3 is a schematic diagram illustrating the ultraviolet lamp device controlled through the regulation-device control circuit of the gas detection module of the present disclosure
Figure 2:
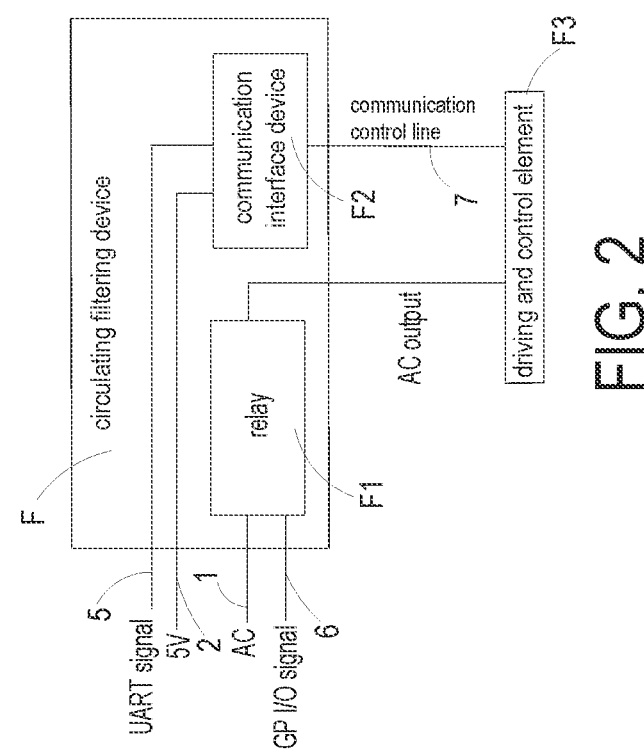
FIG. 2 is a schematic diagram illustrating the circulating filtering device controlled through the regulation-device control circuit of the gas detection module of the present disclosure.

Please refer to FIG. 1, FIG. 2 and FIG. 3. In the embodiment, the AC power line 1 provides an AC voltage. In the embodiment, the AC voltage outputted by the AC power line 1 is inputted to the power converter unit A to convert into a first DC voltage output through a plurality of first voltage dividing lines 2. Notably, in the embodiment, the first DC voltage converted by the first voltage dividing line 2 is 5 V, but not limited thereto. In the embodiment, the first DC voltage converted by the plurality of first voltage dividing lines 2 of the power converter unit A is inputted to the plurality of voltage modulation components B and then modulated to output a second DC voltage through a plurality of second voltage dividing lines 3. Notably, in the embodiment, the second DC voltage converted by the second voltage dividing line 3 is 3.3 V, but not limited thereto.

In the embodiment, the microcontroller unit (MCU) C is connected to the second voltage dividing line 3 of the voltage modulation component B, and the second DC voltage modulated by the second voltage dividing line 3 is inputted to the microcontroller unit C for operation. The microcontroller unit (MCU) C includes at least one expansion port D, a data transmission line 5 and an input and output control line 6. In the embodiment, each of the plurality of expansion ports D is connected to a sensing element a to input a serial communication (IIC) signal to the microcontroller unit (MCU) C through a plurality of serial communication lines 4 connected thereto for calculation, and a Universal Asynchronous Transceiver and Transceiver (UART) signal and a General Purpose Input and Output (GP I/O) signal are outputted for regulation. The data transmission line 5 outputs a plurality of the Universal Asynchronous Transceiver and Transceiver (UART) signals for transmitting to an ultraviolet (UV) lamp device E, at least one external regulation device F, a wireless communication module G and a communication interface device H connected thereto. The input and output control line 6 outputs the General Purpose Input and Output (GP I/O) signal for transmitting to the connected ultraviolet (UV) lamp device E and the at least one external regulation device F. Notably, in the embodiment, the sensing element a connected with the expansion port D is a particle sensing element 1*a* for detecting the air pollution data of suspended particles (PM1, PM2.5, PM10) in the indoor, but not limited thereto. In the embodiment, the sensing element a connected with the expansion port D is a temperature sensing element 2*a* for detecting the air pollution data of the temperature and humidity in the indoor, but not limited thereto. In the embodiment, the sensing element a connected with the expansion port D is a carbon dioxide ($CO_2$) sensing element 3*a* for detecting the air pollution data of carbon dioxide ($CO_2$) in the indoor, but not limited thereto. In the embodiment, the expansion port D can be expanded and connected to a plurality of different sensing elements for detect the information and properties of indoor air pollution. Preferably but not exclusively, the sensing element a is a volatile organic compound (VOC) sensing element 4*a* for detecting the air pollution data of the volatile organic compounds (TVOC). Preferably but not exclusively, the sensing element a is a formaldehyde sensing element for detecting the air pollution data of the formaldehyde (HCHO) gas. Preferably but not exclusively, the sensing element a is a bacteria sensing element 6*a* for detecting the air pollution data of the bacteria. Preferably but not exclusively, the sensing element a is a fungus sensing element 7*a* for detecting the air pollution data of the fungus. Preferably but not exclusively, the sensing element a is virus sensing element 8*a* for detecting the air pollution data of the virus. Preferably but not exclusively, the sensing element a is an ozone ($O_3$) sensing element 9*a* for detecting the air pollution data of the ozone ($O_3$) in the indoor. Preferably but not exclusively, the sensing element a is a carbon monoxide (CO) sensing element 10*a* for detecting the air pollution data of carbon monoxide (CO) in the indoor.

In the embodiment, the wireless communication module G is connected to the second voltage dividing line 3 to input the second DC voltage (3.3 V) converted, modulated and outputted therefrom according to a required DC voltage, and cooperates with the microcontroller unit (MCU) C to output the Universal Asynchronous Transceiver and Transceiver (UART) signal and the General Purpose Input and Output (GP I/O) signal for controlling activation and externally receiving communication signals. Furthermore, the wireless communication module G has two-way communication with the cloud computing service device (not shown) of the indoor air cleaning system.

In the embodiment, the communication interface device H is connected to the first voltage dividing line 2 to input the first DC voltage (5 V) converted, modulated and outputted therefrom according to a required DC voltage, and cooperates with the microcontroller unit (MCU) C to output the Universal Asynchronous Transceiver and Transceiver (UART) signal for controlling activation and providing communication connections. Notably, in the embodiment the communication interface device H is connected to a communication control line 8 and a central control system (not shown) for communication connection and transmission. Preferably but not exclusively, a RS485 communication protocol is used for communication connection and transmission.

In the embodiment, the ultraviolet (UV) lamp device E is connected to input the AC voltage outputted by the AC power line 1 and cooperates with the microcontroller unit (MCU) C to output the General Purpose Input and Output (GP I/O) signal for controlling activation and regulation. In the embodiment, as shown in FIG. 3, the ultraviolet (UV) lamp device E includes a relay E1, and the relay E1 is connected to input the AC voltage outputted from the AC power line 1 and cooperatively connected to the microcontroller unit (MCU) C to output the General Purpose Input and Output (GP I/O) signal, so that the AC voltage is outputted and provided to a power switch E2, and the power switch E2 is connected to control starting and regulation of an ultraviolet (UV) lamp E3.

In the embodiment, the external regulation device F is connected to input the AC voltage outputted by the AC power line 1, connected to the first voltage dividing line 2 to input the first DC voltage (5 V) converted therefrom according to a required DC voltage, and cooperates with the microcontroller unit (MCU) C to output the Universal Asynchronous Transceiver and Transceiver (UART) signal and the General Purpose Input and Output (GP I/O) signal for controlling activation and regulation. Notably, as shown in FIG. 2, the external regulation device F is a circulating filtering device, and the circulating filtering device includes a relay F1 and a communication interface device F2. Preferably but not exclusively, the relay F1 is electrically connected to input the AC voltage outputted by the AC power line 1 and cooperatively connected to the microcontroller unit (MCU) C to output the General Purpose Input and Output (GP I/O) signal, so that the AC voltage is outputted and provided to a driving and control element F3 of the circulating filtering device for power control and regulation. Moreover, the communication interface device F2 is connected to input the first DC voltage (5 V) converted by the first voltage dividing line 2 according to the required DC voltage, cooperating with the microcontroller unit (MCU) C to input the Universal Asynchronous Transceiver and Transceiver (UART) signal outputted therefrom, and connected to the driving and control element F3 for communication connection and transmission through a communication control line 7 to regulate a wind speed of a fan (not shown) of the circulating filtering device. Preferably but not exclusively, a RS485 communication protocol is used for communication connection and transmission. Moreover, in the embodiment, the regulation-device control circuit of the gas detection module is further connected with a plurality of the external regulation devices F, and each of the external regulation devices F includes an address encoder for connection with the input and output control line 6, so that the plurality of external regulation devices F are serially connected for regulation.

In summary, the present disclosure provides a regulation-device control circuit of a gas detection module, which is combined with the devices on each indoor cleaning device to implement air pollution detection and coordinate the regulation operations. Moreover, the control instructions are generated in the cloud computing service device to feed back to the gas detection module for electrical connection, and then transmitted to the driving and control element of the indoor cleaning device to regulate the device for starting operations. It allows the air pollution to pass therethrough for filtration, so that the gas state in the indoor field has the air pollution to be cleaned completely to meet the clean room requirements for safe breathing. In addition, the sensing element in the gas detection module autonomously calculating and comparing the air pollution information is connected to and issues the control instruction to the driving and control element the indoor clean device to regulate the starting operation. It allows the air pollution to pass through the filtration, so that the gas state in the indoor field has the air pollution to be cleaned completely to meet the clean room requirements for safe breathing, and an indoor air cleaning system is achieved. The present disclosure includes the industrial applicability and the inventive steps.

What is claimed is:

1. A regulation-device control circuit of a gas detection module, comprising:

an AC power line providing an AC voltage;

a power converter unit, wherein the AC voltage outputted by the AC power line is inputted to the power converter unit to convert into a first DC voltage output through a plurality of first voltage dividing lines;

a plurality of voltage modulation components, wherein the first DC voltage converted by the plurality of first voltage dividing lines of the power converter unit is inputted to the plurality of voltage modulation components and then modulated to output a second DC voltage through a plurality of second voltage dividing lines; and a microcontroller unit (MCU) connected to the second voltage dividing line, wherein the second DC voltage modulated by the second voltage dividing line is inputted to the microcontroller unit for operation, wherein the microcontroller unit comprises:

at least one expansion port, wherein each of the at least one expansion port is connected to a sensing element to input a serial communication (TIC) signal to the microcontroller unit through a plurality of serial communication lines connected thereto for calculation, and a Universal Asynchronous Transceiver and Transceiver (UART) signal and a General Purpose Input and Output (GP T/O) signal are outputted for regulation;

a data transmission line outputting a plurality of the Universal Asynchronous Transceiver and Transceiver (UART) signals for transmitting to an ultraviolet (UV) lamp device, at least one external regulation device, a wireless communication module and a communication interface device connected thereto; and an input and output control line outputting the General Purpose Input and Output (GP I/O) signal for transmitting to the connected ultraviolet lamp device and the at least one external regulation device;

thereby, the wireless communication module is connected to the second voltage dividing line to input the second DC voltage converted, modulated and outputted therefrom according to a required DC voltage, and cooperates with the microcontroller unit to output the Universal Asynchronous Transceiver and Transceiver (UART) signal and the General Purpose Input and Output (GP I/O) signal for controlling activation and externally receiving communication signals, the communication interface device is connected to the first voltage dividing line to input the first DC voltage converted, modulated and outputted therefrom according to a required DC voltage, and cooperates with the microcontroller unit to output the Universal Asynchronous Transceiver and Transceiver (UART) signal for controlling activation and providing communication connections, the ultraviolet (UV) lamp device is connected to input the AC voltage outputted by the AC power line and cooperates with the microcontroller unit to output the General Purpose Input and Output (GP I/O) signal for controlling activation and regulation, and the external regulation device is connected to input the AC voltage outputted by the AC power line, connected to the first voltage dividing line to input the first DC voltage converted therefrom according to a required DC voltage, and cooperates with the microcontroller unit to output the Universal Asynchronous Transceiver and Transceiver (UART) signal and the General Purpose Input and Output (GP I/O) signal for controlling activation and regulation.

2. The regulation-device control circuit of the gas detection module according to claim 1, wherein the first DC voltage converted by the first voltage dividing line is 5 V.

3. The regulation-device control circuit of the gas detection module according to claim 1, wherein the second DC voltage converted by the second voltage dividing line is 3.3 V.

4. The regulation-device control circuit of the gas detection module according to claim 1, wherein the sensing element is a particle sensing element.

5. The regulation-device control circuit of the gas detection module according to claim 1, wherein the sensing element is a temperature sensing element.

6. The regulation-device control circuit of the gas detection module according to claim 1, wherein the sensing element is a carbon dioxide sensing element.

7. The regulation-device control circuit of the gas detection module according to claim 1, wherein the sensing element is a volatile organic compound sensing element.

8. The regulation-device control circuit of the gas detection module according to claim 1, wherein the sensing element is a formaldehyde sensing element.

9. The regulation-device control circuit of the gas detection module according to claim 1, wherein the sensing element is a bacteria sensing element.

10. The regulation-device control circuit of the gas detection module according to claim 1, wherein the sensing element is a fungus sensing element.

11. The regulation-device control circuit of the gas detection module according to claim 1, wherein the sensing element is a virus sensing element.

12. The regulation-device control circuit of the gas detection module according to claim 1, wherein the sensing element is an ozone ($O_3$) sensing element.

13. The regulation-device control circuit of the gas detection module according to claim 1, wherein the sensing element is a carbon monoxide (CO) sensing element.

14. The regulation-device control circuit of the gas detection module according to claim 1, wherein the communication interface device is connected to a communication control line and a central control system for communication connection and transmission.

15. The regulation-device control circuit of the gas detection module according to claim 14, wherein a RS485 communication protocol is used for communication connection and transmission.

16. The regulation-device control circuit of the gas detection module according to claim 1, further comprising a plurality of the external regulation devices, wherein each of the external regulation devices comprises an address encoder for connection with the input and output control line, so that the plurality of external regulation devices are serially connected for regulation.

17. The regulation-device control circuit of the gas detection module according to claim 1, wherein the external regulation device is a circulating filtering device, and the circulating filtering device comprises a relay and a communication interface device, wherein the relay is electrically connected to input the AC voltage outputted by the AC power line and cooperatively connected to the microcontroller unit to output the General Purpose Input and Output (GP I/O) signal, so that the AC voltage is outputted and provided to a driving and control element of the circulating filtering device for power control and regulation, wherein the communication interface device is connected to input the first DC voltage converted by the first voltage dividing line according to the required DC voltage, cooperating with the microcontroller unit to input the Universal Asynchronous Transceiver and Transceiver (UART) signal outputted therefrom, and connected to the driving and control element for communication connection and transmission through a communication control line to regulate a wind speed of a fan of the circulating filtering device.

18. The regulation-device control circuit of the gas detection module according to claim 17, wherein a RS485 communication protocol is used for communication connection and transmission.

19. The regulation-device control circuit of the gas detection module according to claim 1, wherein the ultraviolet lamp device comprises a relay, and the relay is connected to input the AC voltage outputted from the AC power line and cooperatively connected to the microcontroller unit to output the General Purpose Input and Output (GP I/O) signal, so that the AC voltage is outputted and provided to a power switch, wherein the power switch is connected to control starting and regulation of an ultraviolet lamp.

\* \* \* \* \*